United States Patent
Hung et al.

(10) Patent No.: US 7,636,076 B2
(45) Date of Patent: Dec. 22, 2009

(54) FOUR-COLOR TRANSFLECTIVE COLOR LIQUID CRYSTAL DISPLAY

(75) Inventors: Kuo-Yung Hung, Hsinchu (TW);
Chih-Ming Chang, Jhongli (TW);
Chih-Jen Hu, Jhongli (TW);
Chih-Chun Pei, Hsinchu (TW);
Chih-Hao Chen, Tianjhong Township, Changhua County (TW)

(73) Assignee: Au Optronics Corporation, Hsinchu (TW)

( * ) Notice: Subject to any disclaimer, the term of this patent is extended or adjusted under 35 U.S.C. 154(b) by 628 days.

(21) Appl. No.: 11/233,850

(22) Filed: Sep. 22, 2005

(65) Prior Publication Data

US 2007/0063945 A1     Mar. 22, 2007

(51) Int. Cl.
*G09G 3/36* (2006.01)
*G02F 1/1343* (2006.01)
*G09G 5/00* (2006.01)

(52) U.S. Cl. .................. 345/88; 345/690; 358/516; 382/162

(58) Field of Classification Search ........... 345/87–102, 345/600, 690–694; 358/516; 382/162; 349/143
See application file for complete search history.

(56) References Cited

U.S. PATENT DOCUMENTS

| | | | |
|---|---|---|---|
| 6,724,934 B1 | 4/2004 | Lee et al. | 382/167 |
| 6,876,764 B2* | 4/2005 | Lee et al. | 382/162 |
| 6,897,876 B2 | 5/2005 | Murdoch et al. | 345/589 |
| 7,365,722 B2* | 4/2008 | Lee | 345/88 |
| 2004/0178743 A1 | 9/2004 | Miller et al. | 315/169.3 |
| 2005/0073262 A1* | 4/2005 | Cok | 315/169.3 |
| 2005/0083352 A1 | 4/2005 | Higgins | 345/690 |
| 2005/0099426 A1 | 5/2005 | Primerano et al. | 345/589 |

FOREIGN PATENT DOCUMENTS

| | | |
|---|---|---|
| JP | 09-43604 | 2/1997 |
| JP | 2001-184037 | 7/2001 |
| JP | 2003-248217 | 9/2003 |
| JP | 573284 | 1/2004 |
| JP | 2005-141196 | 6/2005 |
| JP | 2005-338824 | 12/2005 |

* cited by examiner

*Primary Examiner*—Amare Mengistu
*Assistant Examiner*—Seokyun Moon
(74) *Attorney, Agent, or Firm*—Ware, Fressola, Van Der Sluys & Adolphson, LLP

(57) ABSTRACT

The pixel in a transflective color LCD panel of the present invention has an additional sub-pixel area. The pixel is divided into three or more color sub-pixels in R, G, B and at least one sub-pixel M. Each of the color sub-pixels is divided into a transmission area and a reflection area to display color image data. The sub-pixel M can be entirely reflective or partially reflective for displaying a further image data. Two or more algorithms are used to compute the further image data based on the color image data. A selector is used to select one of the algorithms for displaying the further image data. The algorithm selection can be used by a user or automatically selected according to the brightness of ambient light. The transflective LCD panel can be used in a reflective mode when the ambient light reaches a brightness level.

18 Claims, 13 Drawing Sheets

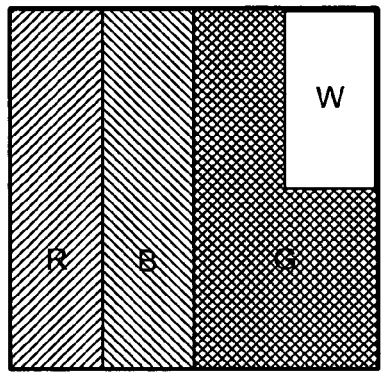
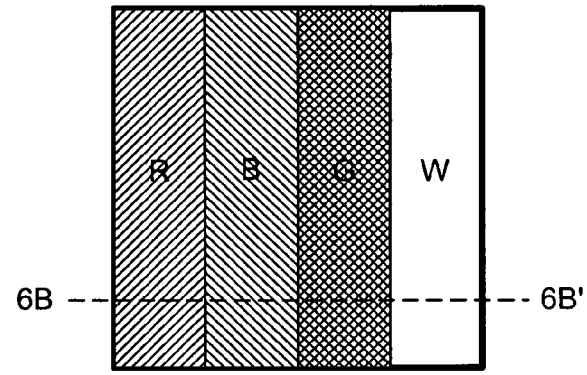
FIG. 5A                FIG. 5B
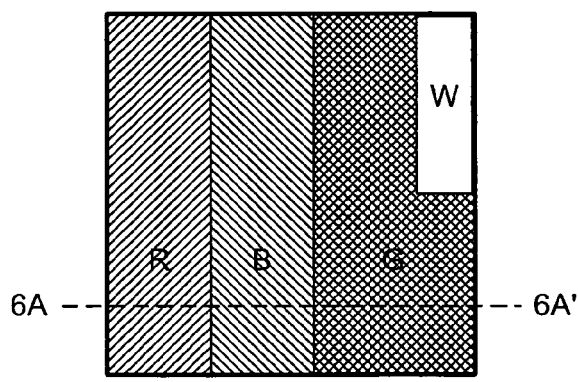
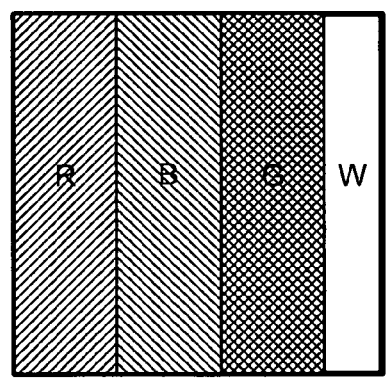
FIG. 5C                FIG. 5D

FOUR-COLOR TRANSFLECTIVE COLOR LIQUID CRYSTAL DISPLAY

CROSS REFERENCE TO RELATED APPLICATIONS

The present application is related to patent application Ser. No. 11,321,011, assigned to the assignee of the present invention.

FIELD OF THE INVENTION

The present invention relates generally to a liquid crystal display panel and, more particularly, to a transflective-type liquid crystal display panel.

BACKGROUND OF THE INVENTION

Due to the characteristics of thin profile and low power consumption, liquid crystal displays (LCDs) are widely used in electronic products, such as portable personal computers, digital cameras, projectors, and the like. Generally, LCD panels are classified into transmissive, reflective, and transflective types. A transmissive LCD panel uses a back-light module as its light source. A reflective LCD panel uses ambient light as its light source. A transflective LCD panel makes use of both the back-light source and ambient light.

As known in the art, a color LCD panel 1 has a two-dimensional array of pixels 10, as shown in FIG. 1. Each of the pixels comprises a plurality of sub-pixels, usually in three primary colors of red (R), green (G) and blue (B). These RGB color components can be achieved by using respective color filters. FIG. 2A illustrates a plan view of a pixel 10 in a conventional transflective liquid crystal panel. The pixel 10 is divided into three color sub-pixels 12R, 12G and 12B and each sub-pixel can be divided into a transmission area (TA) and a reflection area (RA). The pixel 10 is associated with a gate line, Gate n. The color sub-pixels 12R, 12G and 12B are separately associated with data lines $Data_R$ m, $Data_G$ m and $Data_B$ m. The color filter for use with a pixel 10 is shown in FIG. 2B. In FIG. 2B, the color filter has three color filter sections R, G, B corresponding to the color sub-pixels 12R, 12G, 12B of the pixel 10. A cross sectional view of a color sub-pixel 12 is shown in FIG. 3. As shown, the color sub-pixel 12 has an upper layer structure, a lower layer structure and a liquid crystal layer 900 disposed between the layer structures. The upper layer structure comprises an upper substrate 810, a color filter 820 and an upper electrode 830. The lower layer structure comprises a lower substrate 870, a device layer 860, a passivation layer 850 and an electrode layer. The electrode layer comprises a reflective electrode 842 in the reflection area electrically connected to the device layer through a via 852, and a transmissive electrode 844 in the transmission area electrically connected to the reflective electrode 842. The transmissive electrode 844 and the upper electrode are made from a transparent material such as indium-tin oxide (ITO). The reflective electrode 842 also serves as a reflector and is made from one or more highly reflective metals such as Al, Ag, Cr, Mo, Ti and AlNd.

If the overall reflectivity in the reflection areas is insufficient to produce a desired color density, voids or colorless filters within the color filter sections in the reflection areas are used to increase the reflectivity, as shown in FIG. 2B. With this color correction method, the color image quality of the LCD panel may not be desirable.

It is thus advantageous and desirable to provide a method and a sub-pixel structure for use in a transflective color LCD panel for increasing the reflectivity in the pixel without unduly degrading the color quality of the panel.

SUMMARY OF THE INVENTION

The pixel in a transflective color LCD panel of the present invention has an additional sub-pixel area. According to the present invention, a pixel is divided into a plurality of sub-pixels. At least three of the sub-pixels are color sub-pixels in R, G, B and at least one of the sub-pixels is a sub-pixel M. Each of the color sub-pixels R, G and B is divided into a transmission area and a reflection area. The sub-pixel M can be entirely reflective or partially reflective. The color filter for use in the pixel comprises R, G, B color filter segments corresponding to the R, G, B color sub-pixels and possibly a filter segment for the sub-pixel M. The filter segment for the sub-pixel M can be entirely colorless or partially colorless. Furthermore, one or more of the R, G, B color filer segments associated with the reflection area may have a colorless sub-segment.

Preferably, the number of sub-pixels is four, with three sub-pixels being color sub-pixels in R, G and B and one pixel being the sub-pixel M. However, it is possible to have six sub-pixels in a pixel. Among these six sub-pixels, one is the sub-pixel M and five are color sub-pixels, for example. It is also possible to have eight sub-pixels. Among these eight sub-pixels, two are sub-pixels M and six are color sub-pixels in R, G and B, for example.

The colorless sub-segment is referred to as the white sub-segment W, which can be used to control the brightness and the color quality of the display panel. The color signal provided to the sub-segment W is computed based on the color signals provided to the R, G, B color sub-segment. In particular, the present invention uses two or more algorithms to compute the W color signal so that one of the algorithms can be used based on the brightness of the environment, on the preference of a user or on a predetermined criterion.

Alternatively, the "colorless sub-segment" is used to provide a non-primary color and the color signal provided to this sub-segment is yellow, magenta, cyan or the combination thereof.

The present invention will become apparent upon reading the description taken in conjunction with FIGS. 4A-13C.

BRIEF DESCRIPTION OF THE DRAWINGS

FIG. 4A shows a pixel wherein the areas of the sub-pixels R, G, B and M are substantially the same, and the reflection areas in those sub-pixels are also substantially equal to each other.

FIG. 4B shows a pixel wherein the areas of the sub-pixels R, G, B and M are substantially the same, but the reflection area in the sub-pixel M is larger than the reflection area in sub-pixels R, G and B.

FIG. 4C shows a pixel wherein the area of the sub-pixels R, G, B and M are substantially the same, but the sub-pixel M is entirely reflective.

FIG. 4D shows a pixel wherein the areas of the sub-pixels R, G, B and M are substantially the same, but the reflection area in the sub-pixel M is smaller than the reflection area in sub-pixels R, G and B.

FIG. 4E shows a pixel wherein the areas of the sub-pixels R, G, B and M are substantially the same, but the reflection area in the sub-pixel M and the reflection area in sub-pixel G are different from the reflection area in sub-pixels R and B.

FIG. 4F shows a pixel wherein the area of the sub-pixel M is smaller than the area of the sub-pixels R, G, B and the sub-pixel M is partially reflective.

FIG. 4G shows a pixel wherein the area of the sub-pixel M is smaller than the area of the sub-pixels R, G, B and the sub-pixel M is entirely reflective.

FIG. 4H shows a pixel wherein the areas of the sub-pixels R, G, B and M are substantially the same, but the reflection area in the sub-pixel M is larger than the reflection area in sub-pixels R, G and B and the sub-pixel M is located between two color sub-pixels.

FIG. 5A-5G are schematic representations showing various color filters for use in the sub-pixel structures, according to the present invention, wherein a color filter is divided into three color filter segments R, G, B and a fourth filter segment.

FIG. 5A shows a color filter wherein the areas of the color filter segments R, G, B and the fourth filter segment are substantially the same, and the fourth filter segment is partially colorless.

FIG. 5B shows a color filter wherein the areas of the color filter segments R, G, B and the fourth filter segment are substantially the same, and the fourth filter segment is entirely colorless.

FIG. 5C shows a color filter wherein the area of the fourth filter segment is smaller than the area of the color filter segments R, G, B, and the fourth filter segment is partially colorless.

FIG. 5D shows a color filter wherein the area of the fourth filter segment is smaller than the area of the color filter segments R, G, B, and the fourth filter segment is entirely colorless.

FIG. 5E shows a color filter wherein the color filter in the reflection area has three color filter sections of R, G, B and a fourth section of colorless filter, whereas the color filter in the transmission area has only three color filter sections of R, G and B.

FIG. 5F shows a color filter wherein the areas of the color filter segments R, G, B and the fourth filter segment are substantially the same, and the fourth filter segment is partially colorless and wherein the filter segment is located between two color filter segments.

FIG. 5G shows a color filter wherein one or more of the R, G, B color filter segments associated with the reflection area of the pixel may have a colorless sub-segment.

FIGS. 12D-12H are schematic representations of a sub-pixel structure wherein a pixel is divided into eight sub-pixels with each of six sub-pixels being divided into a transmission area and a reflection area and the remaining two sub-pixels being partially reflective or totally reflective, wherein:

FIG. 12D shows each of the remaining two sub-pixels being divided into a transmission area and a reflective area, similar to the other six sub-pixels;

FIGS. 12E and 12G show each of the remaining two sub-pixels being totally reflective; and FIGS. 12F and 12H show each of the remaining two sub-pixels being partially reflective with its reflection area being larger than that in the other six sub-pixels.

DETAILED DESCRIPTION OF THE INVENTION

The pixel in a transflective color LCD panel of the present invention uses at least one additional sub-pixel having a colorless (W) filter segment and a reflective electrode associated with that filter segment. Alternatively, the additional sub-pixel has a filter segment in a non-primary color such as yellow, magenta, cyan or a combination thereof. According to the present invention, a pixel is divided into a plurality of sub-pixels, wherein at least three of the sub-pixels are color sub-pixels in R, G, B and at least one of sub-pixels is a sub-pixel M. Each of the color sub-pixels R, G and B is divided into a transmission area and a reflection area. Accordingly, each of the color sub-pixels R, G, B has a transmissive electrode in the transmission area and a reflective electrode in the reflection area. The sub-pixel M can be entirely reflective or partially reflective. Thus, the sub-pixel M may or may not have a transmissive electrode. The color filter for use in the pixel comprises R, G, B color filter segments corresponding to the R, G, B color sub-pixels and a filter segment for the fourth sub-pixel. The filter segment for the fourth sub-pixel can be entirely colorless or partially colorless. The filter segment for the fourth sub-pixel can be at least partially in a non-primary color, such as yellow, magenta, cyan or a combination thereof.

Figure 1:
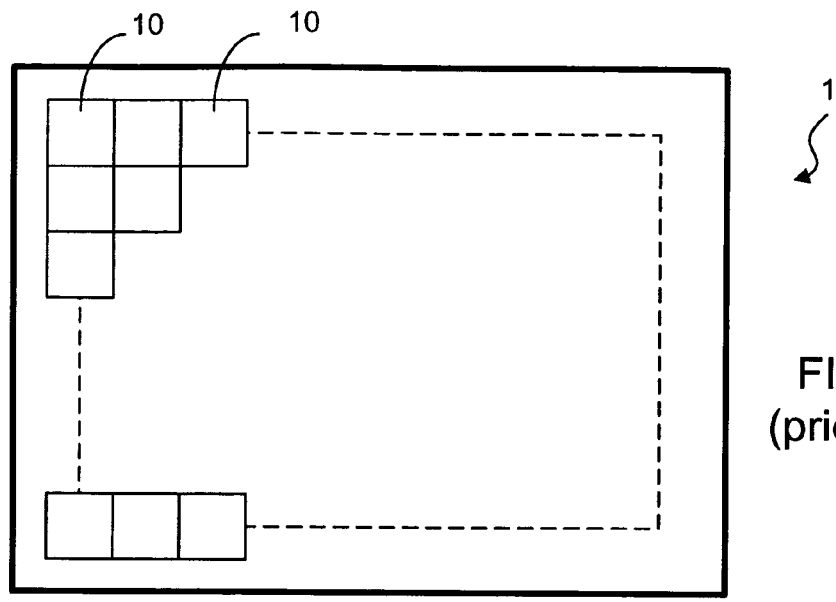
FIG. 1 is a schematic representation of a typical LCD panel.
Figure 3:
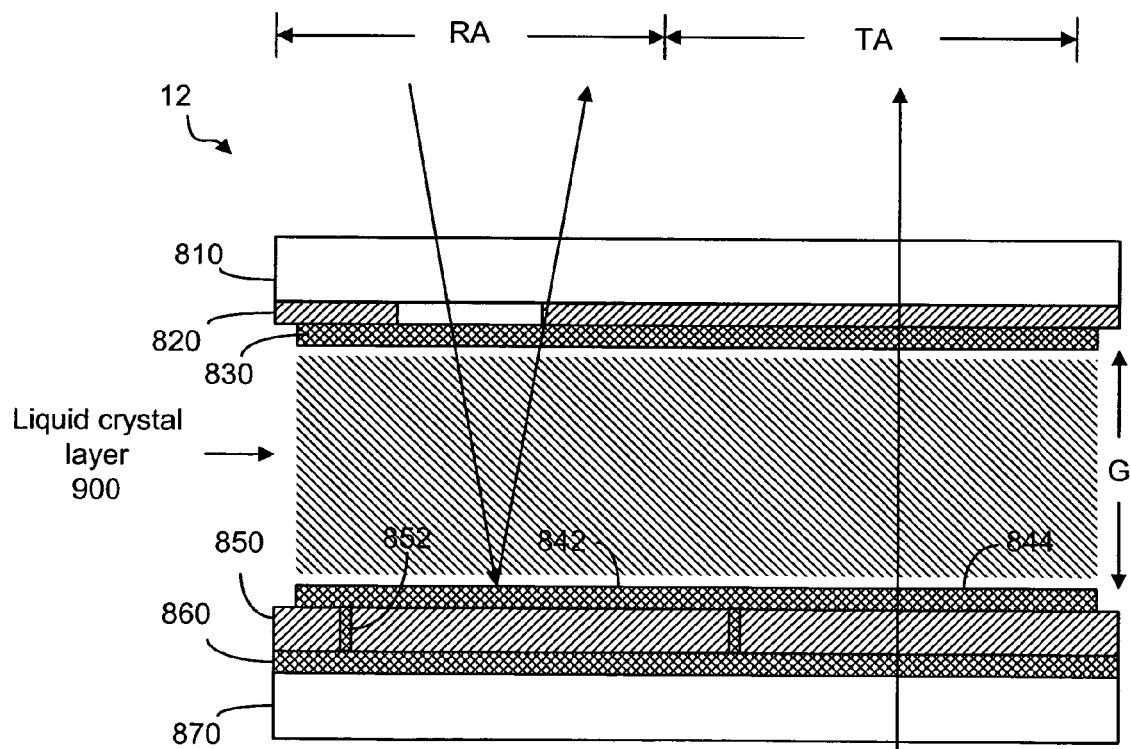
FIG. 3 is schematic representation showing a cross sectional view of a sub-pixel in the conventional transflective LCD panel, and the reflection and transmission of light beams in the sub-pixel.
Figure 2A:
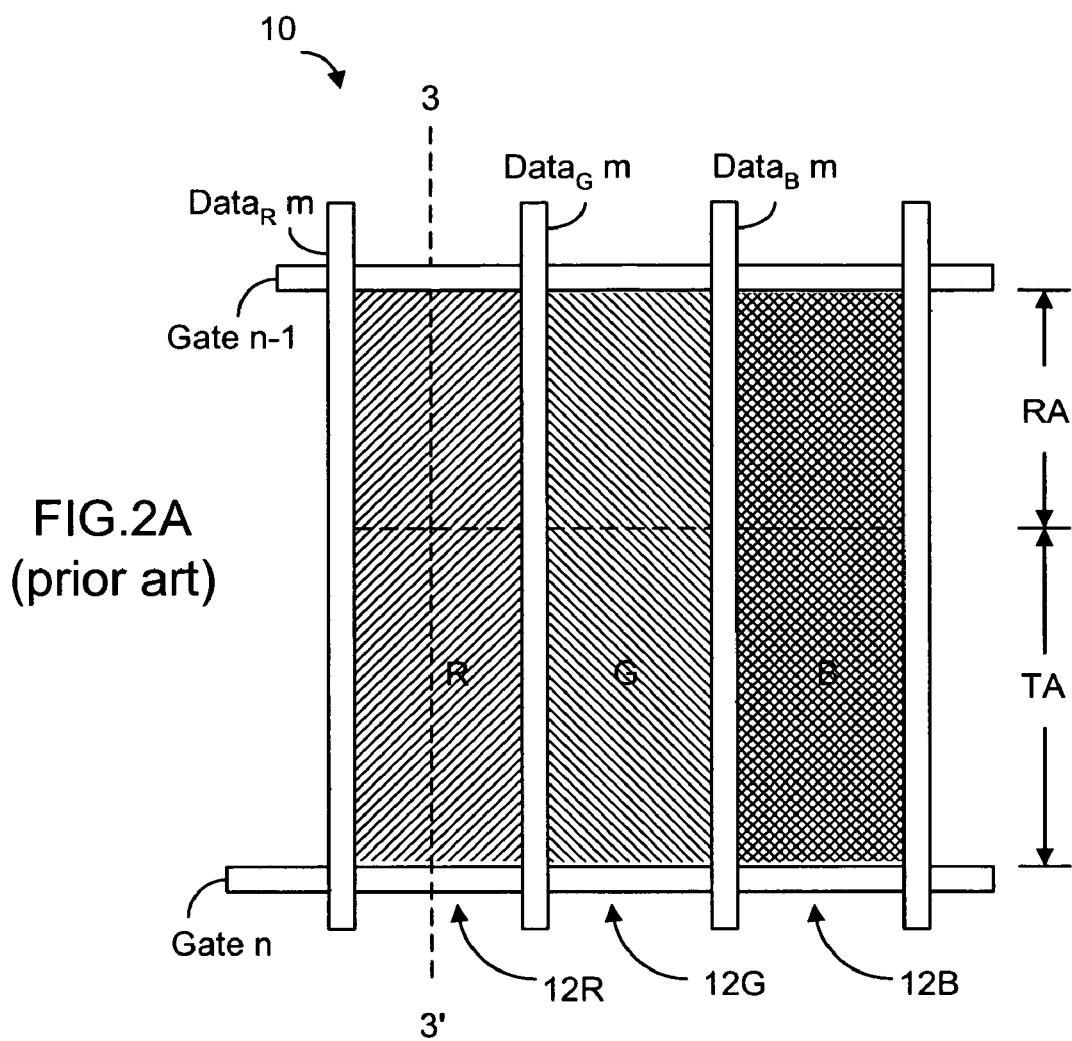
FIG. 2A is a schematic representation showing a plan view of the pixel structure of a conventional transflective color LCD panel.
Figure 2B:
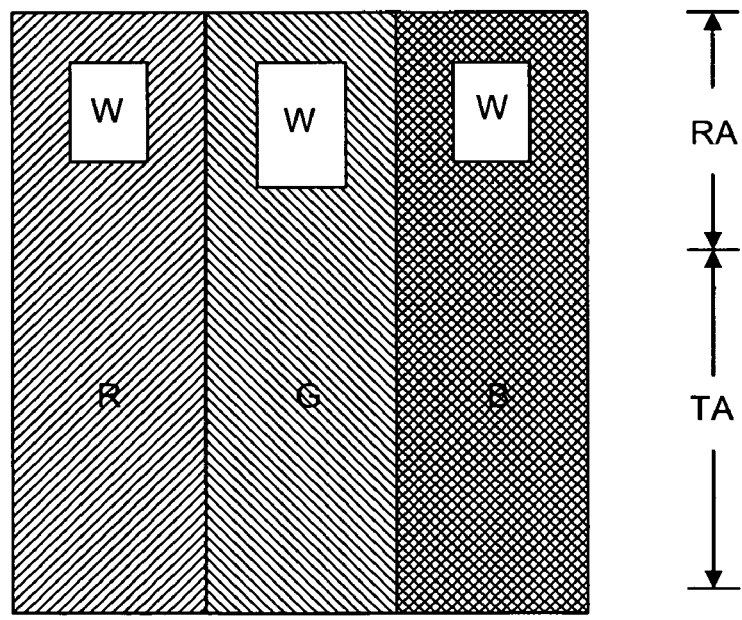
FIG. 2B is a schematic representation showing a color filter for use with a pixel in a conventional transflective color LCD panel.
Figure 4A:
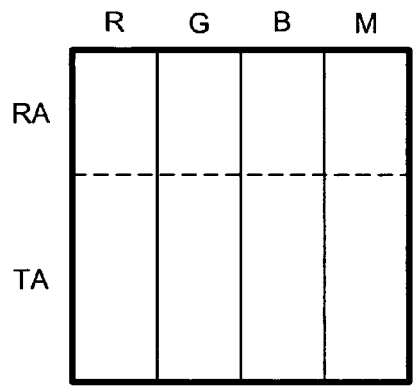
FIG. 4A-4H are schematic representations of various sub-pixel structures, according to the present invention, wherein a pixel is divided into three color sub-pixels R, G, B and a fourth sub-pixel M and wherein each of the color sub-pixels R, G, B is divided into a transmission area and a reflection area.
Figure 4B:
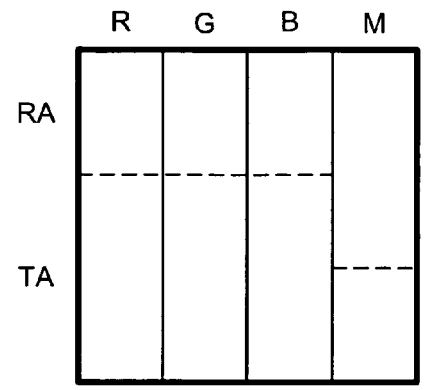
Figure 4C:
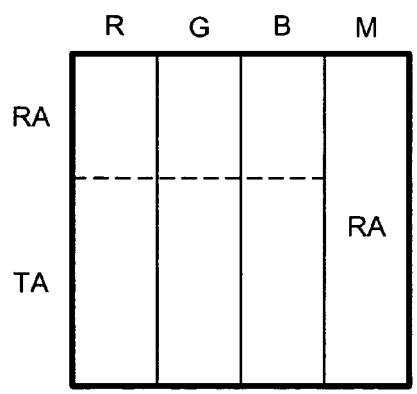
Figure 4D:
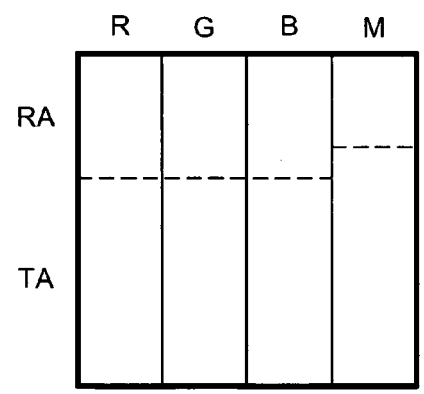
Figure 4E:
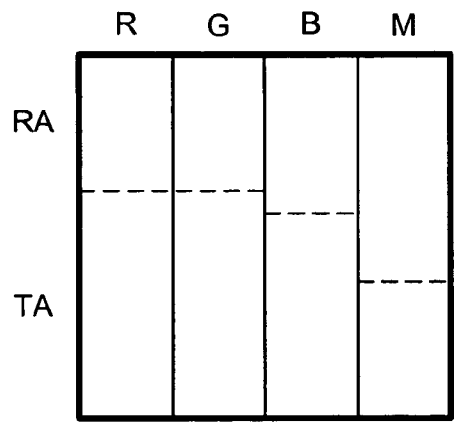

Because there are numerous combinations in the sizes and in the arrangement of electrodes and filter segments in the sub-pixel M, the embodiments disclosed herein and associated drawings are only examples for illustration purposes. In general, a pixel is divided into four sub-pixels R, G, B and M. As shown in FIGS. 4A-4H, each of the color sub-pixels R, G, B is divided into a transmission area and a reflection area, but the sub-pixel M can be entirely or partially reflective. As shown in FIG. 4A, the areas of the sub-pixels R, G, B and M are substantially the same, and the reflection areas in those sub-pixels are also substantially equal to each other. In FIG. 4B, the areas of the sub-pixels R, G, B and M are substantially the same, but the reflection area in the sub-pixel M is larger than the reflection areas in sub-pixels R, G and B. In FIG. 4C, the sub-pixel M is entirely reflective. In FIG. 4D, the reflection area in the sub-pixel M is smaller than the reflection area in sub-pixels R, G and B. In FIG. 4E, the sub-pixels R, G, B and M are substantially the same, but the reflection area in the sub-pixel M and the reflection area in sub-pixel B are larger than the reflection areas in sub-pixels R and G. It is noted that the arrangement of sub-pixels as shown is for illustrative purpose only, and other arrangements are possible. For example, the reflection area in the sub-pixel M and the reflection area in sub-pixel G are larger than the reflection areas in sub-pixels R and B.

Figure 4F:
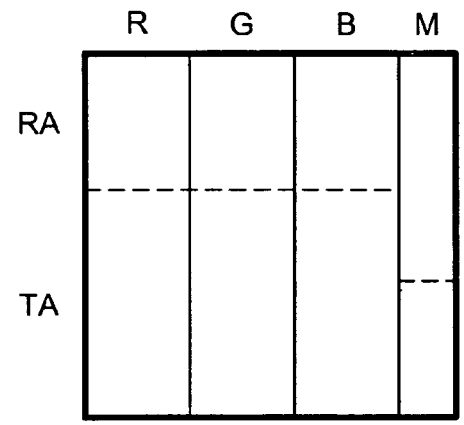
Figure 4G:
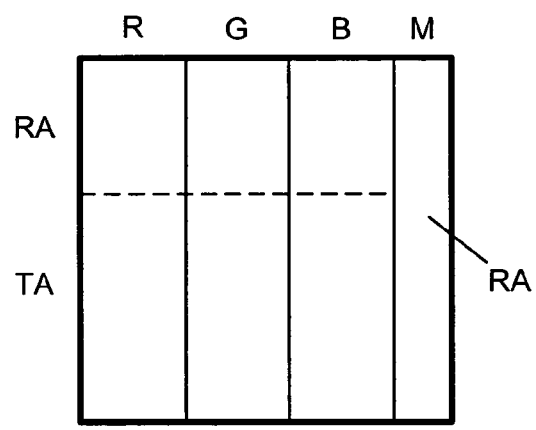
Figure 4H:
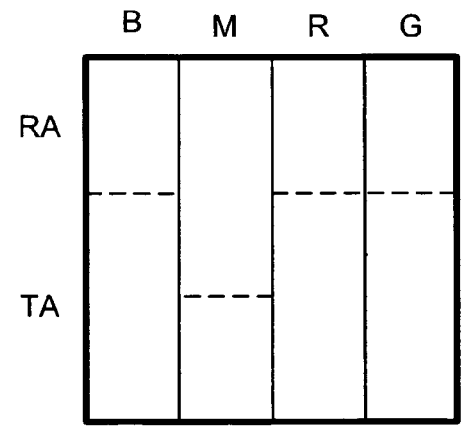

The pixel structures as shown in FIGS. 4F and 4G are essentially the same as those shown in FIGS. 4B and 4C except that the area of sub-pixel M is smaller than the area of the color sub-pixels. In FIG. 4H, sub-pixel M is located between two of the color sub-pixels.

Figure 5E:
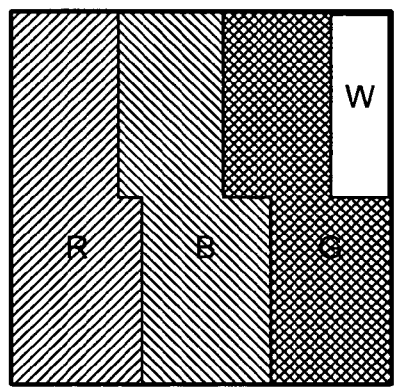
Figure 5F:
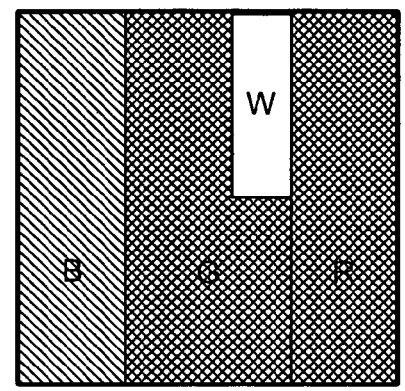

The color filter for use in a pixel as shown in FIGS. 4A to 4H can have many different designs. In general, the color filter must have three color filter segments in R, G, B, each corresponding to a color sub-pixel. The color filter also has a fourth filter segment. The fourth filter segment can be partially colorless, as shown in FIGS. 5A, 5C, 5E and 5F, but it can be entirely colorless (transparent, W), as shown in FIGS. 5B and 5D. The width of the fourth filter segment is generally the same as the width of the fourth sub-pixel M (see FIGS. 4A-4H). In a color filter where the fourth filter segment is partially colorless, the color of the remaining part of the fourth filter segment can be R, G or B. For example, the color of the remaining part is G, as shown in FIGS. 5A and 5C. In FIGS. 5A, 5C, 5E and 5F, the color combination in the fourth filter segment is W/G. However, the color combination can also be W/B or W/R. Alternatively, the letter W is used to represent a non-primary color, such as yellow, magenta, cyan or a combination thereof.

Figure 6A:
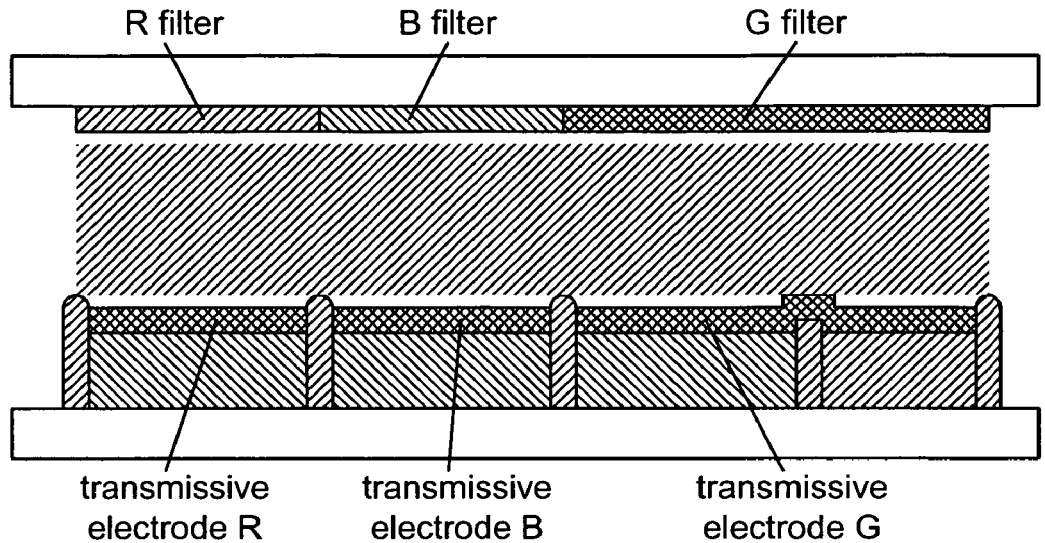
FIG. 6A is a schematic representation showing a cross sectional view of a pixel with three transmissive electrodes.

In a pixel where the fourth filter segment is partially colorless as shown in FIGS. 5A, 5C, 5E, and 5F, the transmission area of the pixel has three transmissive electrodes and one of these transmissive electrode is electrically connected to the transmissive electrode for the fourth sub-pixel. For example, when the color of the remaining part of the fourth filter segment is G, then the transmissive electrode for the fourth sub-pixel (M) is electrically connected to the transmissive electrode for the G sub-pixel, as shown in FIG. 6A. Accordingly, three switching elements (TFTs) are used to control the liquid crystal layers associated with the R, B and G/M transmissive electrodes.

Figure 5G:
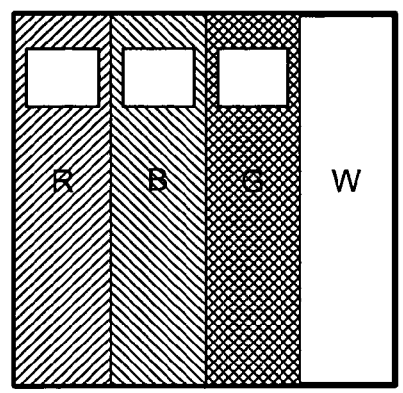

In a different embodiment, the fourth filter section is entirely colorless and one or more of the color filter segments in R, G and B associated with the reflection area (see FIGS. 4A, 4B, 4C, 4D, 4E and 4H) have a colorless sub-segment. For example, all three color filter segments in R, G and B associated with the reflection area have a colorless sub-segment, as shown in FIG. 5G. The colorless sub-segments can be equal in size to each other or different in size.

Figure 6B:
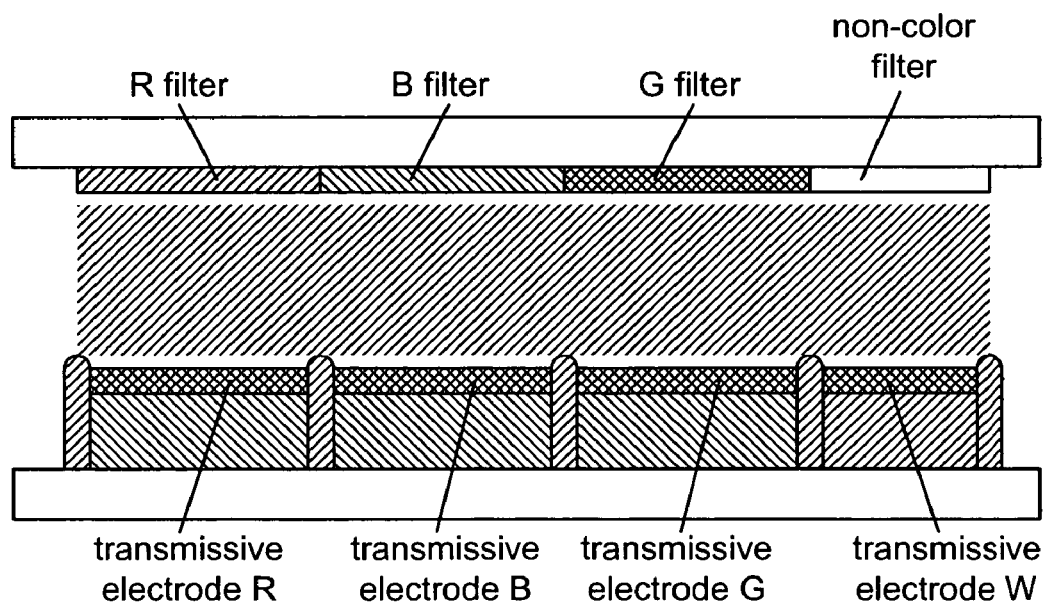
FIG. 6B is a schematic representation showing a cross sectional view of a pixel with four transmissive electrodes.

In a pixel where the fourth filter segment is entirely colorless (W) as shown in FIGS. 5B, 5D and 5G, the transmission area has four transmissive electrodes such that each of the transmissive electrodes is separately controlled by a switching element. The four separate transmissive electrodes for R, B, G and W are shown in FIG. 6B.

Figure 6C:
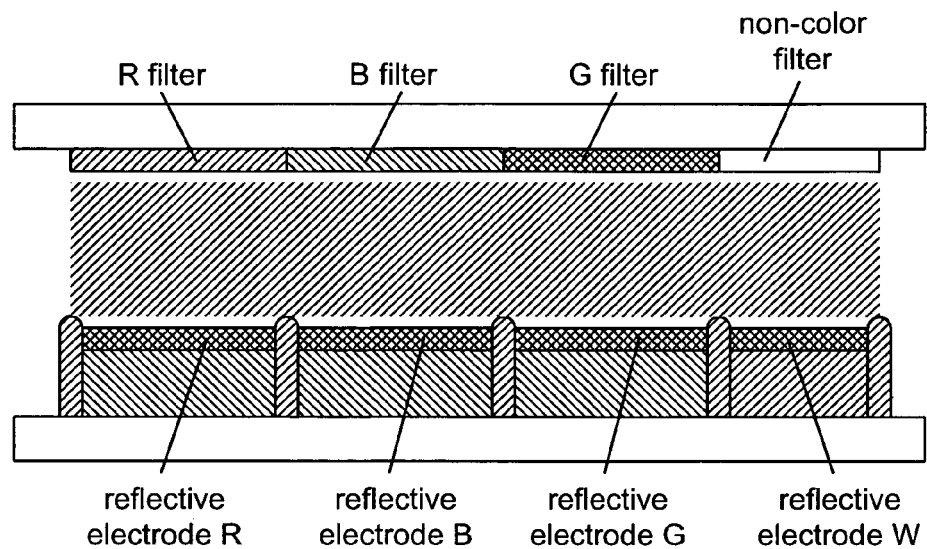
FIG. 6C is a schematic representation showing a cross section view of a pixel with four reflective electrodes.

As shown in FIGS. 5A-5G, there is a W sub-segment in the reflection area. Thus, the reflection area has four reflective electrodes such that each of the reflective electrodes is separately controlled by a switching element. The four separate reflective electrodes for R, B, G and W are shown in FIG. 6C.

Figure 7:
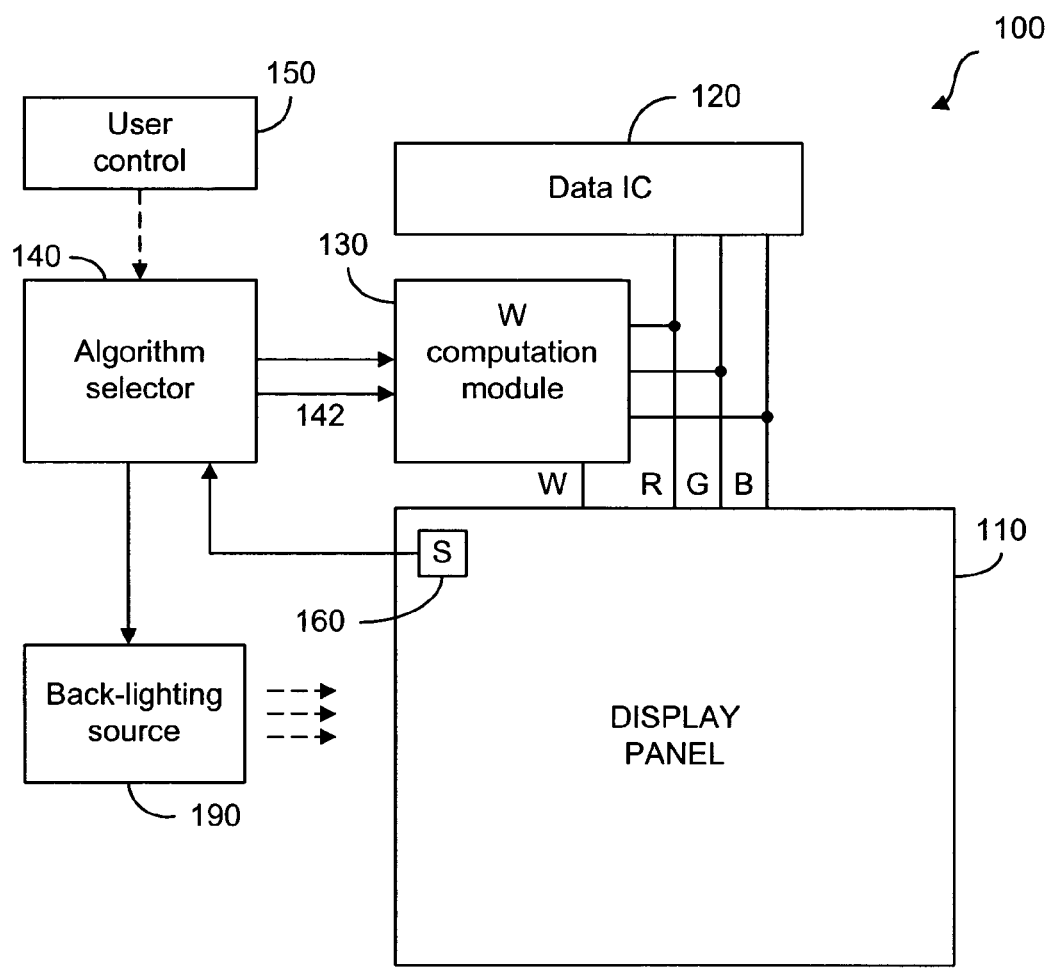
FIG. 7 is a block diagram showing various components in the display system, according to the present invention.

The data signal in the M sub-segment, according to the present invention, is calculated from the data signals for R, G and B with a number of algorithms. As such, the brightness or color quality of the display panel can be improved. FIG. 7 is a block diagram showing a display system, according to the present invention. As shown in FIG. 7, the display system 100 comprises a transflective LCD panel 110 driven by one or more Gate driver ICs (not shown). The image data in three colors, R, G, B, is provided by one or more Data IC 120, which provides the color image data to the LCD panel 110. A back-lighting source 190 is used to provide the image brightness in the transmission mode of the LCD panel 110.

The data signal for the M sub-segment is provided by a computation module 130. The computation module 130 may have two or more algorithms (see FIG. 8) to compute the M data signal. The display system 100 may comprise an algorithm selector 140 to select one of the algorithms. The selection can be made by a user through a wired or wireless control 150 or by the optical sensor signal 160.

For example, the M data signal can be computed based on a linear relationship with the data signal for each of the color components. In the algorithm as shown below, the M data signal is a weighted sum of the data signals R, G and B:

$$M = \alpha R + \beta G + \gamma B, \quad (1)$$

with α being in the range of about 0.08 to about 0.4, β being in the range of about 0.3 to about 0.8 and γ being in the range of about 0.1 to about 0.3. It is preferred that $$\alpha + \beta + \gamma = 1 \quad (2).$$

However, the sum α+β+γ can be smaller or greater than 1. According to Equation 1, even when one or two of R, G, B color image data signals are equal to zero, M is always greater than zero.

In another algorithm, the M data signal has an exponential relationship with the data signal for each of the color components, for example. As shown below, the data signal for each of the color components is modified by an exponential index gamma>1. The range of gamma can be between 1 and 4, for example.

$$Y_{RGB} = T_{Rmax}(R/\mathrm{MAX})^{gamma} + \quad (3)$$
$$Y_{Gmax}(G/\mathrm{MAX})^{gamma} + Y_{Bmax}(B/\mathrm{MAX})^{gamma}$$

$$M = \mathrm{MAX} * \left(\frac{Y_{RGB}}{Y_{RGBMAX}}\right)^{1/gamma}$$

where $Y_{Rmax}$, $Y_{Gmax}$ and $Y_{Bmax}$ are the maximum brightness levels of the display; and $Y_{RGBMAX}$ is the sum of $Y_{Rmax}$, $Y_{Gmax}$, $Y_{Bmax}$. In a display where the brightness level of each color is expressed in the number of bits, n, the maximum brightness level is $2^n$. MAX is the maximum input signal level expressed in gray scale. If the gray scale is expressed in the number of bits, m, then MAX is equal to $2^m$. In the above equations, R, G, B are input digital data for the color components. According to Equation 3, even when one or two of the R, G, B color image data signals are equal to zero, M is always greater than zero.

Figure 10:
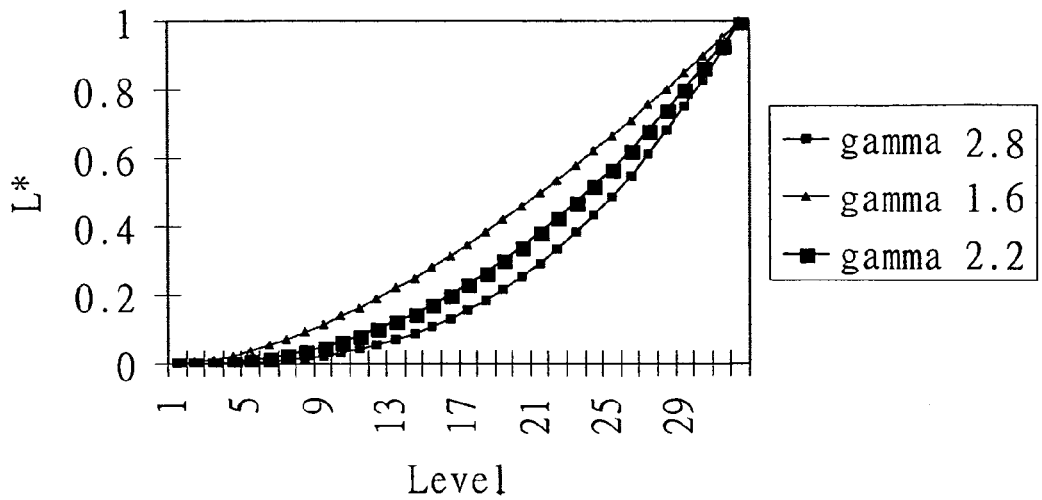
FIG. 10 shows a relationship between brightness level and gray level for different gamma curves.
Figure 11:
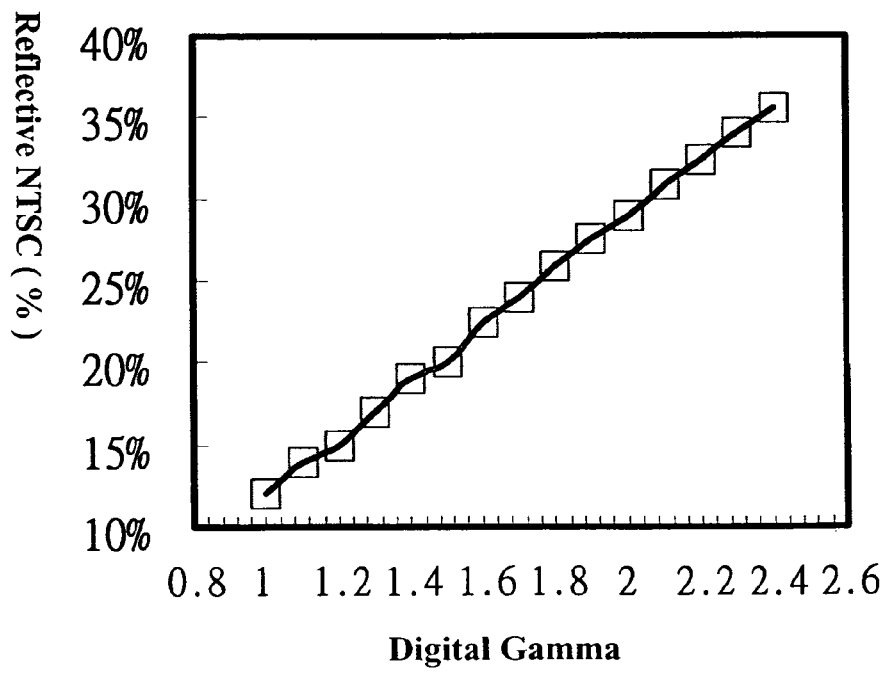
FIG. 11 shows a simulated relationship between reflective NTSC and digital gamma.

Preferably, the data for the color components $R_0$, $G_0$, $B_0$ provided to the display panel 110 are the same as the input data R, G, B. Furthermore, the gamma voltage for the M sub-pixel can be changed by a gamma voltage generator (not shown) so as to achieve different brightness levels at different gray levels as shown in FIG. 10. As such, a different reflective NTSC can be achieved, as shown in FIG. 11. Reflective NTSC can be measured when the LCD is operated at reflective mode with the back-lighting source is turned off.

Figure 8:
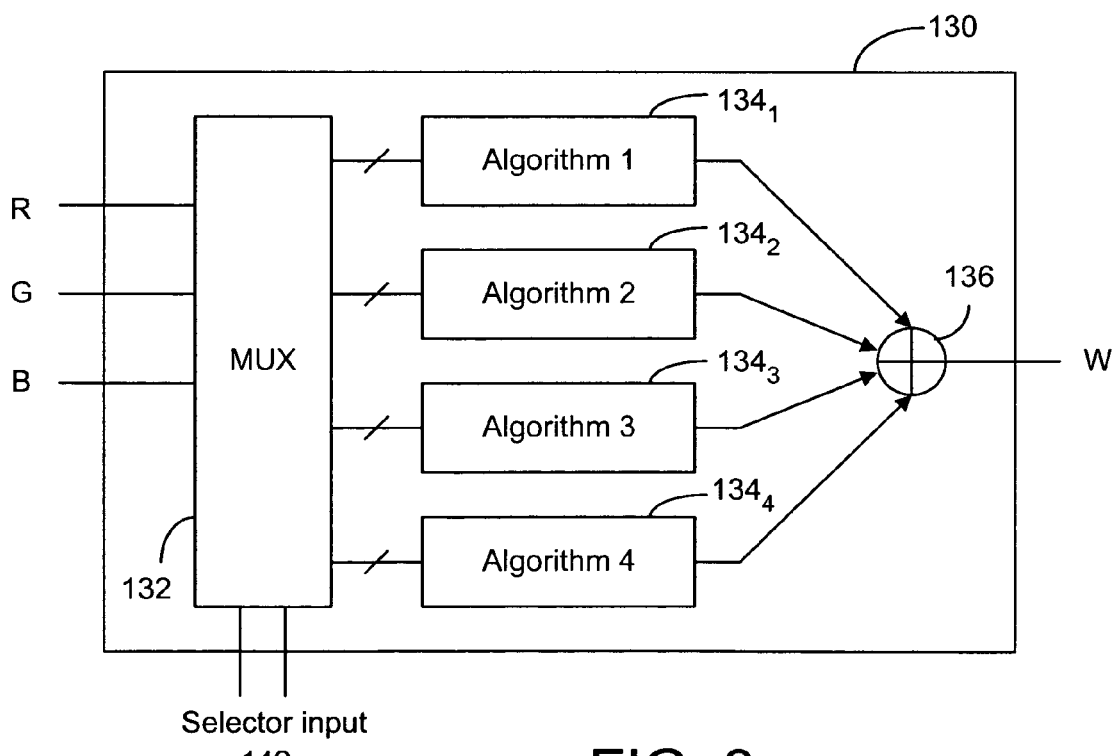
FIG. 8 is a block diagram showing an algorithm selector.

In order to compute the W data signal with different algorithms, the computation module 130 can have a number of software or hardware sub-modules 134*i*, with i=1, 2, 3 . . . . These sub-modules can be selected through a multiplexer 132 under the control of a selector input 142 and the output of the sub-modules can be linked to a summing device 136, as shown in FIG. 8.

It should be noted that a transflective LCD panel is normally used along with a back-lighting source 190 (FIG. 7) so that light from the back-lighting source can be transmitted through the transmissive electrode in the transmission area of each color sub-pixel. In addition, part of the image brightness of the panel is the result of reflection of ambient light by the reflective electrode in the reflection area of each color sub-pixel. When the ambient light is sufficiently low, the transflective LCD panel is essentially operated as a transmissive display panel. When the ambient light is adequate, the transflective display panel uses the transmission mode or the reflection mode. When the ambient light is so strong that the transmission mode becomes insignificant, the back-lighting source can be switched off so that the transflective display panel can be operated as a reflective display panel.

It is possible that the algorithms are selected automatically based on the brightness of the ambient light. For example, a photo-sensor 160 can be placed on or near the display panel 110 to monitor the ambient brightness. The photo-sensor 160 is operatively connected to the algorithm selector 140 for algorithm selection. For example, when the brightness is below a certain level, e.g. 5 kLux, the computation of the M data signal according to Equation 1 may be used. Above the 5 kLux level, Equation 3 may be used. But when the brightness reaches a certain higher level, such as 100 kLux, the back-lighting source 190 can be turned off, and a different algorithm may be used, for example. Thus, the input signal to the fourth sub-pixel can be related to whether the back-lighting source is turned on or turned off.

Figure 9A:
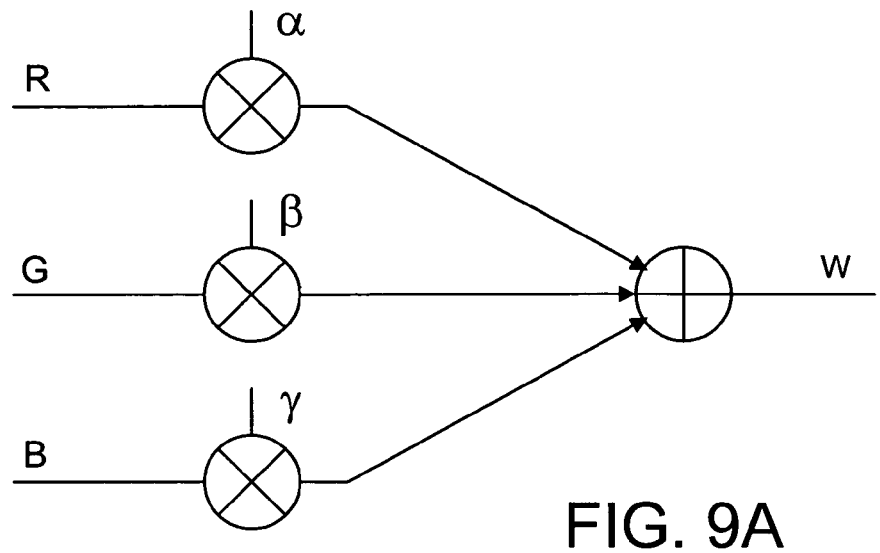
FIG. 9A is a block diagram showing one of the algorithm computation module.
Figure 9B:
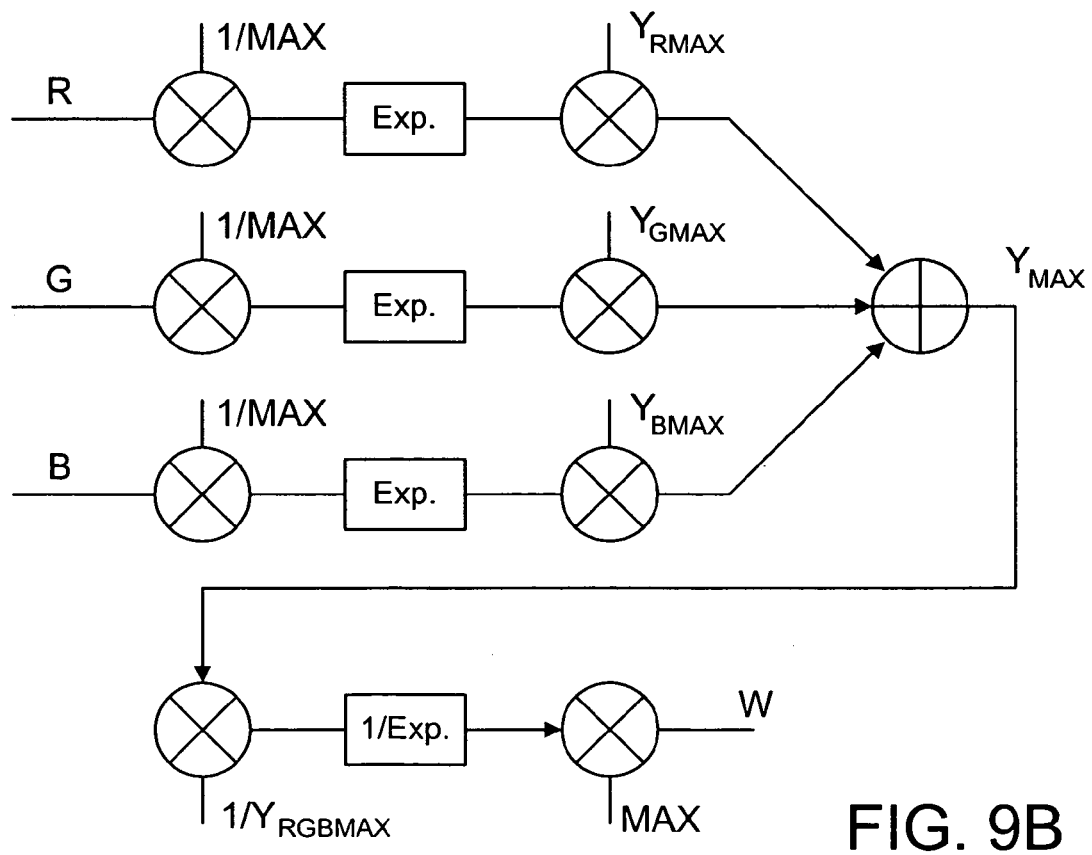
FIG. 9B is a block diagram showing another algorithm computation module.

An exemplary hardware module for computing the M data signal based on Equation 1 is shown in FIG. 9A, and an exemplary hardware module for computing the M data signal based on Equation 2 is shown in FIG. 9B. These hardware modules use known electronic components such as multipliers and summing devices to carry out necessary computation. It is possible that one of the algorithms to be selected in FIG. 8 is M=0. It is also possible to use a separate hardware module to modify the gamma curve of the M sub-segment so that it is different from the gamma curve for the color sub-segments. Gamma curve modification can also be achieved by a look-up table (LUT), for example.

In sum, the present invention uses two or more algorithms to compute an auxiliary data signal based on the data signals for the color sub-pixels in a transflective LCD panel. The auxiliary data signal can be white (W), for example. The auxiliary data signal can be a weighted sum of the data signals for the color sub-pixels in a linear relationship or an exponential relationship. The selection of algorithms can be made by a user, or carried out automatically based on the brightness of the ambient light. Algorithm selection can also be linked to the operation modes of the transflective LCD panel, wherein the transflective LCD panel is operable in a transflection mode, a reflection mode and a transmission mode. The auxiliary data signal can be a non-primary color such as yellow, magenta, cyan or a combination thereof. In that case, one of the algorithms computes the image data for the fourth sub-pixel based on a complementary relationship of the color image data.

Furthermore, even when one or two of the data signals for the color sub-pixels are substantially equal to zero, the auxiliary data signal is greater than zero.

Figure 12A:
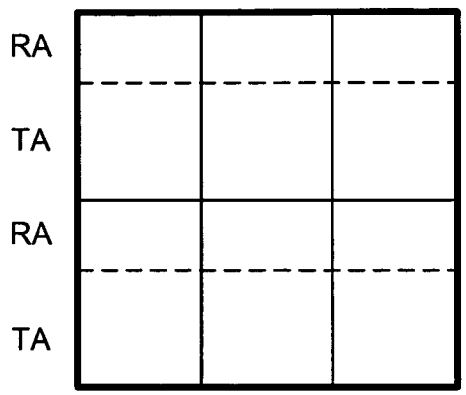
FIG. 12A is a schematic representation of a different sub-pixel structure, according to the present invention, wherein a pixel is divided into six sub-pixels, and wherein each of the sub-pixels is divided into a transmission area and a reflection area.
Figure 12D:
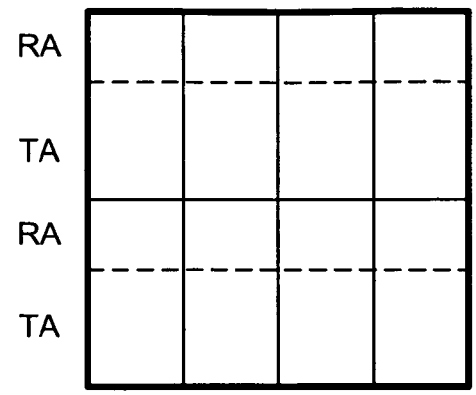
Figure 12B:
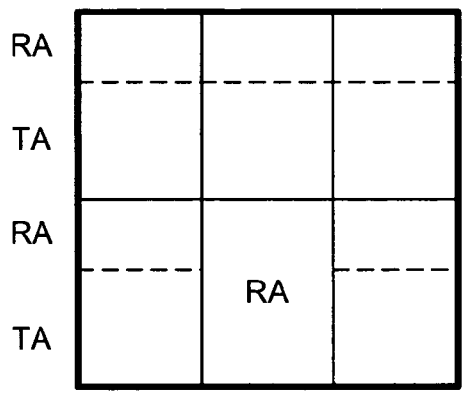
FIG. 12B shows a pixel divided into six sub-pixels, wherein one of the sub-pixel is entirely reflective.

In the preferred embodiment of the present invention, a pixel is divided into four sub-pixels, wherein three of the sub-pixels are color sub-pixels and one is a sub-pixel M. In another embodiment of the present invention, a pixel is divided into six sub-pixels, wherein five of the sub-pixels are color sub-pixels and one is a sub-pixel M (the middle lower sub-pixel). The sub-pixel M can be divided into a transmission area and a reflection area, similar to the other five sub-pixels, as shown in FIG. 12A. However, the sub-pixel M can be totally reflective, as shown in FIG. 12B. Alternatively, the sub-pixel M has a larger reflection area than that in the other five sub-pixels, as shown in FIG. 12C.

Figure 12E:
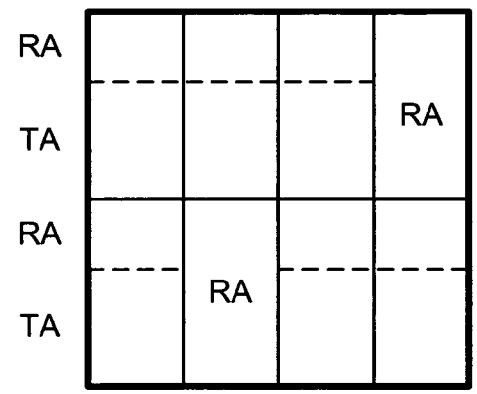
Figure 12F:
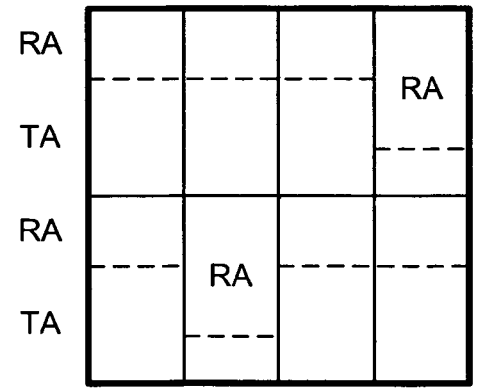
Figure 12G:
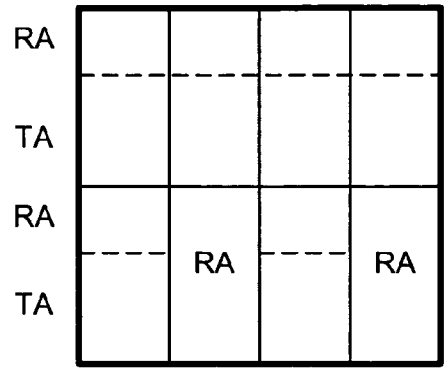
Figure 13A:
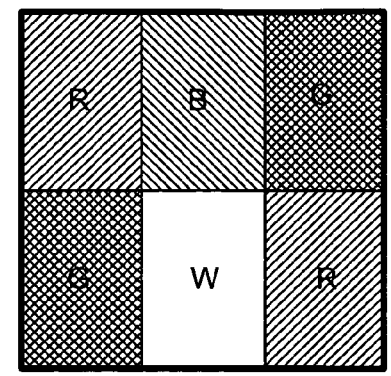
FIG. 13A shows a pixel being divided into six sub-pixels, wherein the filter segment for one of the sub-pixels is colorless.
Figure 12H:
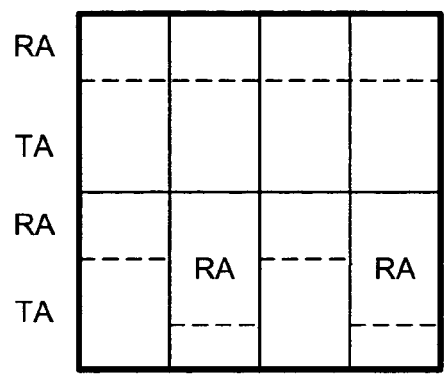
Figure 13B:
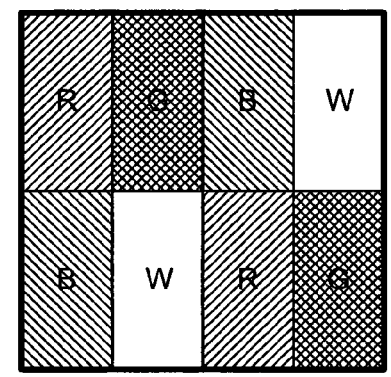
FIG. 13B shows a pixel being divided into eight sub-pixels, wherein the filter segments for two of the sub-pixels are colorless.
Figure 13C:
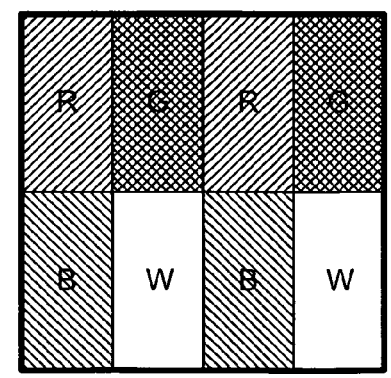
FIG. 13C shows a pixel being divided into eight sub-pixels, wherein the filter segments for two of the sub-pixels are colorless in a different arrangement.

In yet another embodiment of the present invention, a pixel is divided into eight sub-pixels, wherein six of the sub-pixels are color sub-pixels and the remaining two are sub-pixels M (corresponding to the location of filter segments W in FIG. 13B or 13C). Each of the sub-pixels M can be divided into a transmission area and a reflection area, similar to the other six sub-pixels, as shown in FIG. 12D. However, the sub-pixels M can be totally reflective, as shown in FIGS. 12E and 12G. Alternatively, each of the sub-pixels M has a larger reflection area than that in the other six sub-pixels, as shown in FIGS. 12F and 12H.

Figure 12C:
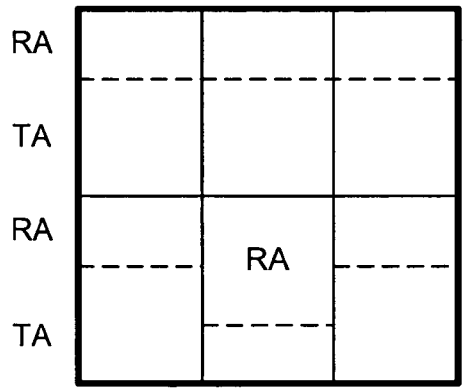
FIG. 12C shows a pixel divided into six sub-pixels, wherein the reflection area in one of the sub-pixel is larger than that in the other sub-pixels.

The color filter associated with the pixel structures as shown in FIG. 12A-12C may comprise a colorless filter segment and five color filter segments, as shown in FIG. 13A. The color filter associated with the pixel structures as shown in FIGS. 12E and 12F may comprise two colorless filter segments and six color filter segments, as shown in FIG. 13B. As shown in FIG. 13B, each of the upper and lower parts of the color filter comprises four different filter segments. The color filter associated with the pixel structures as shown in FIGS. 12G and 12H may comprise two colorless filter segments and six color filter segments, as shown in FIG. 13C. As shown in FIG. 13C, both colorless filter segments are located in the lower part of the color filter.

Thus, although the invention has been described with respect to one or more embodiments thereof, it will be understood by those skilled in the art that the foregoing and various other changes, omissions and deviations in the form and detail thereof may be made without departing from the scope of this invention.

What is claimed is:

1. A display panel comprising:
   a transflective liquid crystal display having a plurality of pixels, comprising:
   a first substrate having a common electrode;
   a second substrate; and
   a liquid crystal layer disposed between the first and second substrate, the liquid crystal layer comprising a plurality of layer segments associated with a plurality of pixels, wherein at least some of the pixels comprise a plurality of sub-pixels and wherein at least three of the sub-pixels are color sub-pixels and at least one of the sub-pixels is a fourth sub-pixel, and wherein each of the color sub-pixels comprises a transmission area having a transmissive electrode disposed on the second substrate and a reflection area having a reflective electrode disposed on the second substrate, and the fourth sub-pixel comprises a further electrode disposed on the second substrate, wherein the further electrode is at least partially reflective;

a data input device to provide color image data to the color sub-pixels;

a computation module to compute further image data for the fourth sub-pixel based on the color image data, the computation module has two or more sub-modules for computing the further image data using different algorithms; and a selector operatively connected to the computation module for selecting the algorithms, wherein one of the algorithms computes the further image data for the fourth sub-pixel based on the color image data modified by an exponential index, wherein said one algorithm has a form of $$Y_{RGB} = Y_{Rmax}(R/\text{MAX})^{gamma} + Y_{Gmax}(G/\text{MAX})^{gamma} + Y_{Bmax}(B/\text{MAX})^{gamma}$$

$$M = \text{MAX} * \left(\frac{Y_{RGB}}{Y_{RGBMAX}}\right)^{1/gamma},$$

where gamma is the exponential index greater than 1; $Y_{Rmax}, Y_{Gmax}$ and $Y_{Bmax}$ are maximum brightness levels of the display for the color sub-pixels; $Y_{RGBMAX}$ is the sum of $Y_{Rmax}, Y_{Gmax}, Y_{Bmax}$; MAX is the maximum input signal level expressed in gray scale; M is the further image data for the fourth sub-pixel and R, G, B are color image data provided to the color sub-pixels.

2. The display panel of claim 1, wherein another one of the algorithms computes the further image data for the fourth sub-pixel to a value substantially equal to zero.

3. The display panel of claim 1, wherein one of the algorithms computes the further image data for the fourth sub-pixel based on a weighted sum of the color image data.

4. The display panel of claim 1, wherein another one of the algorithms has a form of $$M = \alpha R + \beta G + \gamma B,$$

with α being substantially in the range of 0.08 to 0.4; β being substantially in the range of 0.3 to 0.8; and γ being substantially in the range of 0.1 to 0.3, and where M is the further image data for the fourth sub-pixel and R, G, B are color image data provided to the color sub-pixels.

5. The display panel of claim 1, wherein the transflective liquid crystal display is operable in a transflection mode, a reflection mode and a transmission mode, and the further image data can be used in one of the modes.

6. The display panel of claim 1, further comprising means for sensing ambient light so as to allow the selector to select the algorithms based on the sensed ambient light.

7. The display panel of claim 6, further comprising a back-lighting source which is operable in an "ON" state and in an "OFF" state based on the sensed ambient light, wherein the selecting of the algorithms is based on the operated state of the back-lighting source.

8. The display panel of claim 1, wherein when one or two of the color image data of the three color sub-pixels is greater than zero, the further image data for the fourth sub-pixel is greater than zero.

9. The display panel of claim 1, wherein the color image data R, G, B provided to the color sub-pixels are substantially identical to the respective input data to the data input device.

10. The display panel of claim 1, wherein the further electrode is entirely reflective.

11. A method to improve viewing quality of a transflective liquid crystal display having a plurality of pixels, wherein each of at least some of the pixels is partitioned into a plurality of sub-pixels, wherein at least three of the sub-pixels are color sub-pixels and at least one of the sub-pixels is a fourth sub-pixel, each of said color sub-pixels partitioned into a transmission area having a transmissive electrode and a reflection area having a reflective electrode to display color image data, said method comprising the steps of;

providing a further electrode in the fourth sub-pixel to display a further image data, where the further electrode is at least partially reflective;

computing the further image data based on the color image data with two or more algorithms; and selecting one of the algorithms for displaying the further image data, wherein one of the algorithms computes the further image data for the fourth sub-pixel based on the color image data modified by an exponential index, wherein said one algorithm has a form of $$Y_{RGB} = Y_{Rmax}(R/\text{MAX})^{gamma} + Y_{Gmax}(G/\text{MAX})^{gamma} + Y_{Bmax}(B/\text{MAX})^{gamma}$$

$$M = \text{MAX} * \left(\frac{Y_{RGB}}{Y_{RGBMAX}}\right)^{1/gamma},$$

where gamma is the exponential index greater than 1; $Y_{Rmax}, Y_{Gmax}$ and $Y_{Bmax}$ are maximum brightness levels of the display for the color sub-pixels; $Y_{RGBMAX}$ is the sum of $Y_{Rmax}, Y_{Gmax}, Y_{Bmax}$; MAX is the maximum input signal level expressed in gray scale; M is the further image data for the fourth sub-pixel and R, G, B are color image data provided to the color sub-pixels.

12. The method of claim 11, wherein another one of the algorithms sets the further image data for the fourth sub-pixel to a value substantially equal to zero.

13. The method of claim 11, wherein another one of the algorithms computes the further image data for the fourth sub-pixel based on a weighted sum of the color image data.

14. The method of claim 13, wherein said another one of the algorithms has a form of $$M = \alpha R + \beta G + \gamma B,$$

with α being substantially in the range of 0.08 to 0.4; β being substantially in the range of 0.3 to 0.8; and γ being substantially in the range of 0.1 to 0.3, and where M is the further image data for the fourth sub-pixel and R, G, B are color image data provided to the color sub-pixels.

15. The method of claim 11, wherein the transflective liquid crystal display is operable in a transflection mode, a reflection mode and a transmission mode, and the further image data can be used in one of the modes.

16. The method of claim 11, wherein another one of the algorithms computers the further image data for the fourth sub-pixel based on a complementary relationship of the color image data.

17. The method of claim 11, wherein when one or two of the color image data of the three color sub-pixels is substantially equal to zero, the further image date signal for the fourth sub-pixel is greater than zero.

18. The method of claim 11, wherein the further electrode is entirely reflective.

* * * * *

UNITED STATES PATENT AND TRADEMARK OFFICE
CERTIFICATE OF CORRECTION

PATENT NO.       : 7,636,076 B2                                      Page 1 of 1
APPLICATION NO. : 11/233850
DATED            : December 22, 2009
INVENTOR(S)      : Hung et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1084 days.

Signed and Sealed this

Twenty-first Day of December, 2010

David J. Kappos
*Director of the United States Patent and Trademark Office*